United States Patent
Gebhardt et al.

(10) Patent No.: US 7,130,681 B2
(45) Date of Patent: Oct. 31, 2006

(54) USE OF ACCELEROMETER SIGNAL TO AUGMENT VENTRICULAR ARRHYTHMIA DETECTION

(75) Inventors: Ursula Gebhardt, Minneapolis, MN (US); Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 536 days.

(21) Appl. No.: 10/435,174

(22) Filed: May 9, 2003

(65) Prior Publication Data

US 2004/0225332 A1    Nov. 11, 2004

(51) Int. Cl.
*A61B 5/04* (2006.01)
*A61B 5/103* (2006.01)

(52) U.S. Cl. .............. 607/6; 607/14; 600/513; 600/515; 600/587

(58) Field of Classification Search .............. 600/513, 600/515, 518, 519, 587; 607/5, 6, 14
See application file for complete search history.

(56) References Cited

U.S. PATENT DOCUMENTS

| | | | |
|---|---|---|---|
| 3,716,059 A | 2/1973 | Welborn et al. | ........ 128/419 D |
| 4,865,036 A | 9/1989 | Chirife | ............... 128/419 D |
| 5,261,418 A | 11/1993 | Ferek-Petric | |
| 5,304,208 A | 4/1994 | Inguaggiato et al. | |
| 5,342,402 A | 8/1994 | Olson et al. | |
| 5,342,404 A | 8/1994 | Alt et al. | |
| 5,454,838 A | 10/1995 | Vallana et al. | |
| 5,480,412 A | 1/1996 | Mouchawar et al. | |
| 5,496,361 A | 3/1996 | Moberg et al. | |
| 5,540,727 A | 7/1996 | Tockman et al. | |
| 5,545,186 A | 8/1996 | Olson et al. | |
| 5,549,650 A | 8/1996 | Bornzin et al. | |
| 5,549,652 A | 8/1996 | McClure et al. | |
| 5,628,777 A | 5/1997 | Moberg et al. | |
| 5,693,075 A | 12/1997 | Plicchi et al. | |
| 5,941,904 A * | 8/1999 | Johnston et al. | .............. 607/19 |
| 5,987,352 A | 11/1999 | Klein et al. | |
| 5,991,661 A | 11/1999 | Park et al. | |
| 6,009,349 A | 12/1999 | Mouchawar et al. | |
| 6,077,236 A | 6/2000 | Cunningham | |
| 6,128,526 A | 10/2000 | Stadler et al. | |
| 6,249,700 B1 | 6/2001 | Alt | |
| 2003/0045805 A1 | 3/2003 | Sheldon et al. | |

FOREIGN PATENT DOCUMENTS

WO    WO 97/24981    7/1997

* cited by examiner

*Primary Examiner*—Robert Pezzuto
*Assistant Examiner*—Yun Haeng Lee
(74) *Attorney, Agent, or Firm*—Michael C. Soldner; Girma Wolde-Michael

(57) ABSTRACT

A system and method for detecting and discriminating atrial arrhythmias based on mechanical signals of cardiac wall motion and electrical signals of cardiac depolarizations. A mechanical event rate determined from sensed mechanical events is used to corroborate an electrical event rate determined from sensed EGM or ECG signals to classify the heart rhythm. If the event rates are not correlated, other parameterized data from the mechanical signal and electrical signal are evaluated to detect evidence of an arrhythmia. If electrical and mechanical event data do not corroborate a common arrhythmia condition, electrical and mechanical sensing parameters may be adjusted.

15 Claims, 10 Drawing Sheets

USE OF ACCELEROMETER SIGNAL TO AUGMENT VENTRICULAR ARRHYTHMIA DETECTION

FIELD OF THE INVENTION

The present invention relates generally to cardiac arrhythmia detection in an implantable medical device, and more particularly to a method and apparatus for detecting and classifying cardiac rhythms by an implantable medical device based on sensed mechanical and electrical activity of the heart.

BACKGROUND OF THE INVENTION

Implantable cardiac stimulation devices are available for treating cardiac arrhythmias by delivering cardiac stimulation pulses for pacing, cardioverting or defibrillating the heart. Such a device, commonly known as an implantable cardioverter defibrillator or "ICD", senses a patient's heart rhythm and classifies the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT) in addition to bradycardia.

Upon detecting an arrhythmia, the ICD delivers an appropriate therapy. Cardiac pacing is delivered in response to the absence of sensed intrinsic depolarizations, referred to as P-waves in the atrium and R-waves in the ventricle. In response to tachycardia detection, a number of tiered therapies may be delivered beginning with anti-tachycardia pacing therapies and escalating to more aggressive shock therapies until the tachycardia is terminated. Termination of a tachycardia is commonly referred to as "cardioversion." Ventricular fibrillation (VF) is a serious life-threatening condition and is normally treated by immediately delivering high-energy shock therapy. Termination of VF is normally referred to as "defibrillation." With regard to atrial arrhythmias, atrial tachycardia or atrial flutter can be treated with anti-tachycardia pacing therapies, pulse bursts, or a cardioversion shock, and atrial fibrillation is typically treated with pulse bursts or a defibrillation shock.

Reliable ICD performance depends on accurate detection of arrhythmias such that an appropriate therapy may be selected and promptly delivered. Undetected malignant arrhythmias can be fatal, and undetected non-malignant arrhythmias may leave the patient in a hemodynamically compromised state. Inappropriately delivered therapies due to false arrhythmia detections can induce arrhythmias in some patients. It is desirable, therefore, to avoid delivering a therapy due to inappropriate arrhythmia detection. For example, it is undesirable to deliver cardioversion therapy during sinus tachycardia, which is a normal heart rate increase in response to exercise. Furthermore, a cardioversion or defibrillation shock is generally painful to the patient and depletes the battery charge. Therefore, accurate prompt detection of cardiac arrhythmias is critical in the selecting and delivering appropriate arrhythmia therapies.

The most common approach to detecting arrhythmias in implantable automatic cardioverters and defibrillators is based on monitoring sensed event intervals determined from cardiac electrogram (EGM) signals. Monitoring of sensed intervals generally involves identifying the event intervals and event rates as they occur and applying a preset group of criteria, which must be met in order to detect a particular arrhythmia. Criteria for identifying various arrhythmias may all be monitored simultaneously. An arrhythmia detection and classification system generally disclosed in U.S. Pat. No. 5,342,402, issued to Olson et al., incorporated herein by reference in its entirety, uses criteria for sensed events, event intervals, and event rates and is employed in the Medtronic Model 7219 devices. An arrhythmia detection and classification system that employs a prioritized set of inter-related rules for arrhythmia detection is generally disclosed in U.S. Pat. No. 5,545,186, issued to Olson et al., also incorporated herein by reference in its entirety.

The majority of clinical experience in detecting cardiac arrhythmias with regard to implantable automatic cardioverting and defibrillating devices is based on bipolar sensing in the area of the right ventricular apex. New cardiac stimulation therapies and applications, such as cardiac resynchronization therapy, however, may require particular lead locations to achieve targeted stimulation at specific locations. These requirements may counter the optimal location of electrodes for reliable cardiac arrhythmia detection. As the variety of implantable cardiac stimulation devices increases, e.g., devices capable of sensing and stimulating in the left side of the heart with the use of a lead deployed through the coronary sinus or leadless devices implanted in the vicinity of the heart such as in a subaxillary location, the type and reliability of EGM signals available for detecting cardiac arrhythmias may change. Thus, the quality of the EGM signals available for arrhythmia detection may suffer.

Limitations of EGM sensing are well known in the art. Noise in the form of electromagnetic interference, skeletal muscle depolarizations, far-field signals, or polarization artifact following a stimulation pulse can interfere with accurate sensing of intrinsic electrical activity. Oversensing of cardiac activity or noise can result in false detections of cardiac events. Undersensing of cardiac activity can result in missed detections of cardiac events. In either situation, cardiac stimulation therapies may be inappropriately withheld or delivered.

Mechanical sensing of cardiac activity has been proposed for use in cardiac stimulation therapy applications such as optimizing timing intervals during cardiac pacing or monitoring hemodynamic performance. Detection of peak endocardial wall motion in the apex of the right ventricle for optimizing A–V intervals has been validated clinically. A system and method for using cardiac wall motion sensor signals to provide hemodynamically optimal values for heart rate and AV interval are generally disclosed in U.S. Pat. No. 5,549,650 issued to Bornzin, et al. A cardiac stimulating system designed to automatically optimize both the pacing mode and one or more pacing cycle parameters in a way that results in optimization of a cardiac performance parameter, including for example heart accelerations, is generally disclosed in U.S. Pat. No. 5,540,727, issued to Tockman, et al.

An accelerometer-based activity sensor used to provide a signal that corresponds to the acceleration due to the heartbeat of a patient is generally disclosed in U.S. Pat. No. 5,991,661 issued to Park, et al. When the patient is determined to be at rest, the acceleration signal is used to determine parameters indicative of the contractility of the heart and the displacement of the heart during a heartbeat.

Implantable sensors for monitoring heart wall motion have been described or implemented for use in relation to the right ventricle. A sensor implanted in the heart mass for monitoring heart function by monitoring the momentum or velocity of the heart mass is generally disclosed in U.S. Pat. No. 5,454,838 issued to Vallana et al. A catheter for insertion into the ventricle for monitoring cardiac contractility having an acceleration transducer at or proximate the catheter tip is generally disclosed in U.S. Pat. No. 6,077,236 issued to Cunningham. Implantable leads incorporating accelerometer-based cardiac wall motion sensors are generally disclosed in U.S. Pat. No. 5,628,777 issued to Moberg, et al. A device for sensing natural heart acceleration is generally disclosed in U.S. Pat. No. 5,693,075, issued to Plicchi, et al. A system for myocardial tensiometry including a tensiometric element disposed at a location subject to bending due to cardiac contractions is generally disclosed in U.S. Pat. No. 5,261,418 issued to Ferek-Petric et al. All of the above-cited patents are hereby incorporated herein by reference in their entirety.

Thus the use of cardiac wall motion sensors in evaluating cardiac hemodynamic performance is known. The use of the signal from a cardiac wall motion sensor as a primary indicator of potentially malignant cardiac arrhythmias is proposed in the above-cited '361 patent to Moberg. The cardiac wall motion sensor signal may be used with conventional R-wave detection circuitry that relies on an IEGM for measuring cardiac activity. An implantable cardiac stimulating device which uses cardiac displacement signals to detect and discriminate arrhythmias is generally disclosed in U.S. Pat. No. 5,480,412 issued to Mouchawar et al., hereby incorporated herein by reference in its entirety. Cardiac wall acceleration signals provided by a cardiac wall motion sensor are integrated over time to derive cardiac velocity signals, which are further integrated over time to derive cardiac displacement signals.

A need remains, however, for an implantable medical device that is capable of detecting cardiac arrhythmias using mechanical cardiac activity information to augment electrical sensing of cardiac activity and that allows classification of detected arrhythmias for monitoring or therapy selection purposes. An implantable system and algorithm employing both mechanical and electrical cardiac activity information can be used to overcome limitations described that are encountered when relying solely on electrical activity sensing, particularly in newer systems that do not include traditional right ventricular apical EGM sensing.

Furthermore, an implantable medical device capable of evaluating mechanical event signals that allows prompt detection of the transition from hemodynamically stable to hemodynamically unstable arrhythmias is also needed. As indicated above, commercial implementations of lead-based accelerometers have been used in relation to the right ventricle. However, left ventricular wall motion is a more direct correlate to cardiac output than right ventricular wall motion. Therefore, monitoring left ventricular wall motion is expected to be more sensitive in discriminating hemodynamically stable and unstable rhythms.

SUMMARY OF THE INVENTION

The present invention provides a system and method for reliably detecting and classifying cardiac arrhythmias. In particular, the invention correlates electrical signals and mechanical signals of cardiac activity to detect and classify arrhythmias in a manner more reliable than using either electrical or mechanical signals alone.

The system includes electrodes for measuring cardiac electrical signals and a mechanical sensor, preferably an accelerometer, for measuring cardiac mechanical activity. The electrodes and accelerometer may be deployed intra- or extracardially and may be positioned on the same or different leads or contained on or in an implantable medical device included in the system. The implantable medical device includes signal processing circuitry for receiving and processing electrical and mechanical signals and further includes a controller and associated memory for comparing and analyzing sensed signals in an algorithm for classifying the heart rhythm. In one embodiment, a cardiac wall displacement signal is obtained by filtering the accelerometer signal using a high-pass filter and a low-pass filter. The resulting low frequency signal is correlated to cardiac wall displacement. A therapy control and therapy delivery system may also be included to respond to a detected arrhythmia.

In one embodiment, the system includes a second mechanical sensor, which may be located intra- or extracardially but at a different location than a first, primary mechanical sensor. The second mechanical sensor is used as a cross-check sensor for rejecting non-cardiac related motion artifacts that appear on both the first and second mechanical sensor signals.

The algorithm for classifying the heart rhythm uses both electrical and mechanical signals. In one embodiment, an electrical event rate and a mechanical event rate are determined from intervals between sensed electrical events and intervals between sensed mechanical events, respectively. When the signals are correlated such that the electrical and mechanical event rates or event intervals are approximately equal, the heart rhythm is classified according to the measured event rate. If however, the electrical and mechanical event rates are not approximately equal, additional information from the electrical and mechanical signals is evaluated to obtain evidence of an arrhythmia. For example, a fast electrical event rate occurring with absent, low amplitude, or erratic mechanical activity evidences fibrillation. A silent or very erratic electrical signal accompanying an erratic mechanical signal evidences bradycardia or ectopy. If the electrical and mechanical signals do not corroborate each other in detecting and classifying the heart rhythm, adjustments may be made to parameters controlling the sensing operations of one or both signals to correct inaccurate sensing of either signal due to under or oversensing.

In another embodiment, a system and method are provided for monitoring dynamic changes in cardiac wall displacement and acceleration as transitions in the heart rhythm occur. An acceleration measurement parameter is determined from an accelerometer signal for measuring cardiac wall acceleration. A displacement measurement parameter is determined from a displacement signal derived from the acceleration signal for measuring cardiac wall displacement. A displacement signal is preferably obtained by filtering the accelerometer signal using filters that match the low frequency component of the acceleration signal that corresponds to displacement. Acceleration and displacement signals are preferably obtained from an accelerometer positioned in operative relation to the left ventricle such that acceleration and displacement signals are well-correlated to cardiac output. In one embodiment, a coronary sinus lead is equipped with an accelerometer or other mechanical sensor of wall motion for sensing left ventricular basal, free wall or anterior motion.

Arrhythmia detection and classification criteria according to this embodiment include defining thresholds relating to a change in displacement and optionally thresholds relating to acceleration changes, wherein these changes are indicative of transitions between rhythms. The displacement measurement parameter and the acceleration measurement parameter are monitored and compared to the predefined criteria for detecting rhythm changes. In particular, detection of the transition from hemodynamically stable VT to unstable VT/VF is preferably based on criteria including a decreasing acceleration parameter and a displacement parameter that is less than a specified threshold.

In yet another embodiment, displacement and acceleration signals are monitored following the delivery of an arrhythmia therapy for use in measuring a hemodynamic recovery time, re-detecting arrhythmias, and detecting the presence of post-therapy electro-mechanical dissociation (EMD).

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

As indicated above, the present invention is directed toward providing a method and apparatus for detecting and classifying cardiac arrhythmias. The present invention is useful in patient monitoring and in selecting an appropriate cardiac stimulation therapy, or other type of therapy such as a drug therapy, to treat a detected arrhythmia. As such, the present invention may be embodied in an implantable cardiac monitoring system or in an implantable cardiac stimulation or other therapy delivery system.

Figure 1:
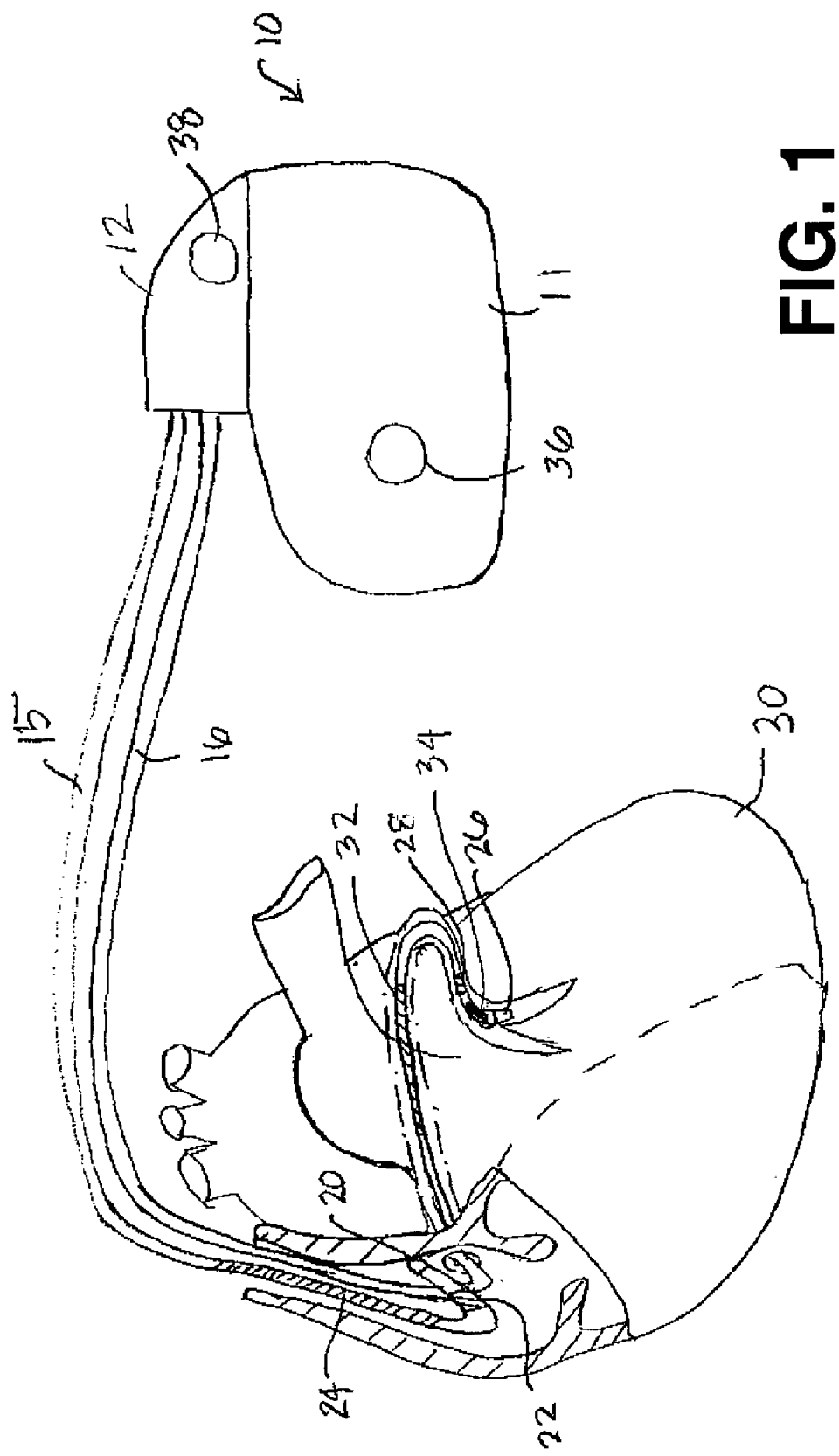
FIG. 1 is an illustration of an implantable medical device in association with a patient's heart.

FIG. 1 is an illustration of an implantable medical device 10 in association with a patient's heart 30. IMD 10 may be configured for both monitoring of and delivering therapy to heart 30. For example, IMD 10 may include a pulse generator to deliver electrical stimulation to heart 30 for use in cardiac pacing therapies, cardioversion or defibrillation. In accordance with the invention, IMD 10 obtains a signal indicative of the dynamic mechanical activity of heart 30 and an electrical signal indicative of electrical activity of the heart.

Using both signals, i.e., the electrical signal and the mechanical signal, IMD 10 detects and classifies the heart rhythm. When both signals indicate an arrhythmia condition, IMD 10 classifies the arrhythmia. The mechanical signal and the electrical signal are used to corroborate each other in the detection of arrhythmias. If an arrhythmia is detected, IMD 10 can be configured to deliver appropriate therapy to restore normal rhythm. The therapy may be electrical stimulation therapy, drug delivery or another therapy intended to treat cardiac arrhythmia. If the electrical and mechanical signals do not corroborate each other in detecting and classifying the heart rhythm, adjustments may be made to parameters controlling the sensing operations of one or both signals to correct inaccurate sensing of either signal due to under or oversensing.

IMD 10 includes a hermetically sealed housing 11 having a connector block assembly 12 for receiving the proximal end of one or more cardiac leads to provide electrical connection between electrodes and associated conductors carried by the cardiac leads to circuitry enclosed within housing 11. In the example of FIG. 1, connector block 12 receives the proximal end of a right atrial lead 15 and a coronary sinus lead 16.

Right atrial lead 15 is positioned such that its distal end is in the vicinity of the right atrium and the superior vena cava (SVC). Lead 15 is shown equipped with a ring electrode 22 and a tip electrode 20 for sensing and/or delivering electrical stimulation pulses in the right atrium. Lead 15 is further equipped with an SVC coil electrode 24 for delivering high-energy shock therapy. The ring electrode 22, the tip electrode 20 and the SVC coil electrode 24 are each connected to an insulated conductor within the body of the right atrial lead 15. Each insulated conductor is coupled at its proximal end to a connector inserted into connector block 12.

The coronary sinus lead 16 is advanced within the vasculature of the left side of the heart via the coronary sinus and great cardiac vein. The coronary sinus lead 16 is shown in the embodiment of FIG. 1 as having a optional defibrillation coil electrode 32 that may be used in combination with SVC coil electrode 23 and/or housing 11 for delivering electrical shocks for cardioversion and defibrillation therapies. Coronary sinus lead 16 is also shown equipped with a distal tip electrode 26 and ring electrode 28 for sensing and/or stimulation functions in the left chambers of the heart. Each electrode 26, 28, and 32 is coupled to an insulated conductor within the body of lead 16. Each insulated conductor provides connection to a proximal connector inserted in connector block 12.

In some embodiments of the present invention, the coronary sinus lead 16 is provided with a mechanical sensor 34 capable of generating a signal proportional to mechanical heart activity, in particular in proportion to left ventricular wall motion. Sensor 34 may be incorporated adjacent tip electrode 26 or at other locations along the body of coronary sinus lead 16 such that sensor 34 is sensitive to cardiac mechanical activity. Sensor 34 is preferably embodied as a uniaxial, biaxial, or triaxial accelerometer contained in a capsule of a relatively small size and diameter such that it may be included in a coronary sinus lead without substantially increasing the lead diameter or impairing the ability to steer the lead to a monitoring site. An accelerometer may be incorporated in a cardiac lead as generally described in U.S. patent application Ser. No. 2003/0045805 to Sheldon et al., incorporated herein by reference in its entirety. Sensor 34 may alternatively be provided as another type of sensor such as an optical, acoustical, or Hall effect sensor or a sensor having piezoelectric, inductive, capacitive, resistive, or other elements which produce a variable signal proportional to heart wall motion or acceleration.

The depicted positions of the leads and electrodes shown in FIG. 1 in or about the right and left heart chambers are approximate and merely exemplary. For example, sensor 34 may alternatively be located on coronary sinus lead 16 such that sensor 34 is positioned in the coronary sinus, in the great cardiac vein, or in any accessible inferior cardiac vein. In one embodiment, a coronary sinus lead equipped with an accelerometer is positioned in the coronary sinus such that the accelerometer is sensitive to the motion of the base of the left ventricle. In other embodiments, a coronary sinus lead equipped with an accelerometer is positioned such that the accelerometer is deployed deeper into the great cardiac vein or anterior veins to assess left free wall or anterior motion. Positioning of a coronary sinus lead-mounted accelerometer may be tailored according to individual patient need.

Furthermore, it is recognized that alternative leads and stimulation/sense electrodes that are adapted for placement at stimulation or sensing sites on, in or relative to the atria and/or ventricles may be used in conjunction with the present invention. For example, epicardial leads may be used in place of or in addition to the endocardial and coronary sinus leads shown in FIG. 1. With respect to the present invention, an accelerometer or other mechanical sensor of cardiac activity may be incorporated in an epicardial lead, endocardial lead, intravenous lead, subcutaneously positioned lead, or submuscularly positioned lead, which may or may not include additional sensors or electrodes. An accelerometer or other wall motion sensor may be positioned as generally described in any of the above-cited patents or as described in U.S. patent application Ser. No. 10/376,981, filed Feb. 28, 2003, entitled "Method and Apparatus for Assessing Left Ventricular Function and Optimizing Cardiac Pacing Intervals Based on Left Ventricular Wall Motion", to Chinchoy, incorporated herein by reference in its entirety.

It is further contemplated that the present invention may be implemented in a leadless system in which a device implanted subcutaneously or sub-muscularly in a position over the heart such as an axillary location could use non-intracardiac lead based methods of electrical and mechanical sensing to detect cardiac arrhythmias and optionally deliver an electrical stimulation or other type of therapy.

IMD 10 is generally shaped to allow subcutaneous or submuscular implantation in the thoracic or abdominal regions. In some embodiments, IMD 10 may be equipped with electrodes arranged on or incorporated in housing 11 and/or connector block 12 to facilitate subcutaneous ECG sensing of cardiac electrical activity. Such sensing electrodes may be arranged substantially as described in U.S. Pat. No. 5,987,352 issued to Klein et al. or U.S. Pat. No. 6,128,526 issued to Stadler et al., both patents incorporated herein by reference in their entirety. In the example of FIG. 1, subcutaneous ECG sensing electrodes 36 and 38 are illustrated as being incorporated in housing 11 and connector block 12, respectively.

While sensor 34 is shown positioned within a cardiac lead in the example of FIG. 1, an accelerometer or other mechanical sensor of cardiac wall motion may alternatively be incorporated on or within housing 11 or connector block 12 for sensing mechanical cardiac activity. In such embodiments, IMD 10 is positioned, for example in a subaxillary location, such that the accelerometer or other type of mechanical sensor is sensitive to motion caused by myocardial contraction, preferably contraction of the left ventricle.

Figure 2:
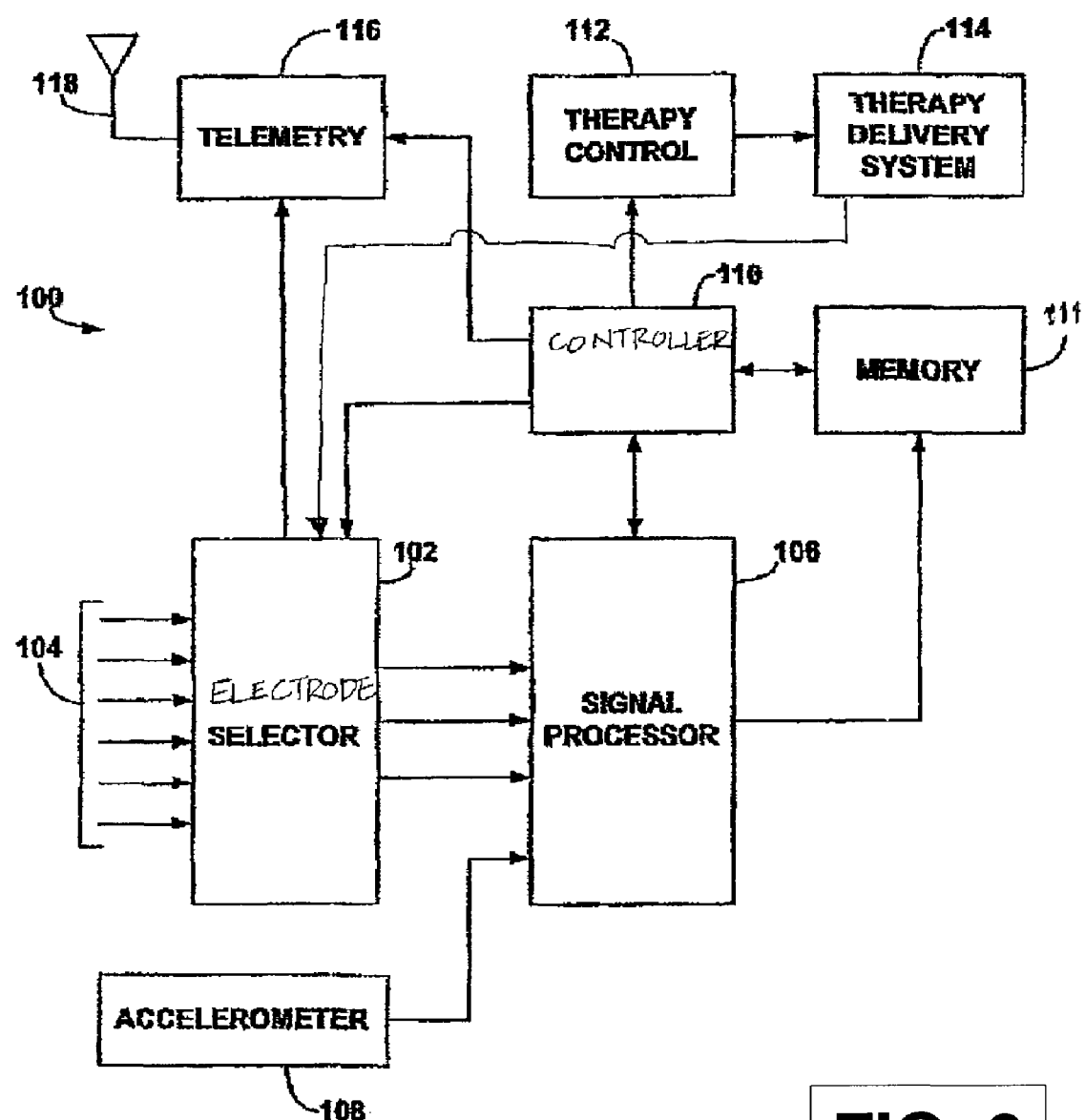
FIG. 2 is a block diagram illustrating a system for detecting cardiac arrhythmias.

FIG. 2 is a block diagram illustrating a system 100 for detecting cardiac arrhythmias. System 100 may include an electrode selector circuit 102 that selects one or more electrode pairs 104, a signal processor circuit 106, an accelerometer 108, a controller 110, memory 111, a therapy control circuit 112, a therapy delivery system 114, and a telemetry circuit 116 with antenna 118. The components of system 100 may be housed in or on a common housing such as that shown in FIG. 1. Alternatively, portions of system 100 may be housed separately. For example some or all of electrode pairs 104 and accelerometer 108 may be positioned on leads extending from a housing as shown in FIG. 1. Particular therapy delivery systems, such as drug delivery systems, may be provided in a separate housing. In this case, therapy control circuit 112 may interact with therapy delivery system 114 via an electrical cable or wireless link.

Controller 110 may take the form of a microprocessor or may alternatively take the form of dedicated digital circuitry or other programmable logic device. Electrode selector circuit 102 may be controlled by controller 110 to select desired electrode pairs for acquisition of electrical signals oriented along one or more vectors relative to the heart. The electrical signals obtained via the electrode pairs 104 can be used to determine a heart rate based on intervals occurring between sensed electrical events such as P-waves or R-waves. With regard to the embodiment shown in FIG. 1, sensing vectors may be selected between a tip and ring electrode, either a tip, ring or coil electrode and the IMD housing, either a tip or ring electrode and a coil electrode, or between the electrodes incorporated on the IMD housing. Signal processor 106 receives output from electrode selector circuit 102 and accelerometer 108. Accelerometer 108, which may be deployed, as described above, i.e., intracardially in an endocardial or coronary sinus lead or extracardially in an epicardial lead, a subcutaneous or submuscular lead or on or within the housing of the IMD, is used to sense mechanical cardiac events.

Signal processor circuit 106 may include a number of sense amplifiers that amplify the ECG or EGM signals as well as the acceleration signal. Signal processor circuit 106 may further include filters for smoothing and/or filtering unwanted signal frequency components. Low-pass, high-pass or band-pass filters may be included having characteristics matched to the expected frequency content of the cardiac electrical and mechanical signals of interest.

In addition, signal processor circuit 106 may include sampling and comparator circuitry for analysis of the electrical signals and heart acceleration signals relative to criteria such as average, peak-to-peak, or total amplitude thresholds. Alternatively, controller 110 may digitally sample the signals amplified by signal processor circuit 106 and perform a software-based analysis of the digital signals. Thus, signal processor circuit 106 may include an analog-to-digital converter that converts the analog signals received from electrode selector circuit 102 and accelerometer 108 into digital samples for analysis by controller 110. Controller 110 may provide the necessary control and clock signals for operation of signal processor circuit 106.

Memory 111 is provided for storage of digital samples produced by signal processor circuit 106 and intermediate data stored and retrieved by controller 110. For example, signal processor circuit 106 may include a number of buffers that hold digital samples for storage in memory 111. Although not illustrated in FIG. 2 for simplicity, controller 110, memory 111, and signal processor 106 may communicate via a common data and instruction bus, as is well known in the art. The digital samples may be parameterized in signal processor circuit 106 or controller 110, to produce values for comparison to a predetermined threshold. Again, the comparison may take place within discrete circuitry included in signal processor circuit 106 or via code executed by controller 110.

ECG or EGM data received from electrode selector circuit 102 can be processed and parameterized to represent a variety of different values useful in the comparison. Generally, ECG or EGM data will be used to determine the heart rate for use in detecting an arrhythmia. Electrical events sensed upon an EGM/ECG signal crossing of a specified sensing threshold or other event threshold or sensing criteria. Intervals between sensed events are compared to one or more specified cycle length thresholds for detection of an arrhythmia, such as tachycardia or fibrillation. Fibrillation and tachycardia detection based on programmable fibrillation and tachycardia detection interval ranges is known in the art. In one embodiment, the electrical signals are further processed to produce an amplitude value, such as an average, peak-to-peak, or total amplitude of a sensed event such as an R-wave or P-wave. During an arrhythmia, the amplitudes of such events may become erratic or even undersensed. Thus, monitoring the variability of electrical event amplitudes, corroborated by mechanical event data, can be useful in detecting and classifying an arrhythmia.

Likewise, heart acceleration data received from accelerometer 108 can be processed and parameterized to represent values used in comparisons to event sensing criteria, arrhythmia detection or classification criteria and for corroborating electrical activity data. In one embodiment, a cardiac rate is determined based on the acceleration data by measuring time intervals between cardiac acceleration events. An acceleration event, for example acceleration corresponding to the ejection phase of ventricular systole, may be sensed by comparing heart acceleration signals to a mechanical event sensing threshold. Time intervals measured between sensed mechanical events can be used for determining a mechanical event rate. These measured intervals or the mechanical event rate may be compared to time intervals measured between sensed electrical events or the electrical event rate, respectively. Thus, mechanical and electrical event interval information may be stored in memory 111 and retrieved by controller 110 for making such comparisons. Time intervals between mechanical events may also be compared to arrhythmia detection criteria. Such criteria may include a threshold interval length and a required number or percentage of intervals meeting the threshold interval length, similar to arrhythmia detection criteria based on EGM or ECG sensing.

The acceleration signals may be further processed to produce an amplitude value, such as an average, peak-to-peak, or total amplitude of a sensed mechanical event. During fibrillation or ectopy, uncoordinated contraction of myocardial fibers can produce small or erratic heart wall accelerations. During ventricular tachycardia, acceleration signals measured using an accelerometer positioned in a coronary sinus lead for detecting cardiac wall acceleration at the base of the left ventricle have been observed in some patients to increase in amplitude compared to sinus rhythm. Thus, monitoring the variability of mechanical event amplitudes, corroborated by electrical event data, can be useful in detecting and classifying arrhythmias.

The acceleration signals may be processed for obtaining a displacement signal that is further processed and parameterized for measuring cardiac wall displacement. A displacement measurement parameter may be compared to an average, peak-to-peak, or total amplitude thresholds for dynamically detecting changes in displacement. An increase in the acceleration signal amplitude during ventricular tachycardia may not always be consistent among patients. However, a decrease in acceleration event amplitudes and a decrease in cardiac wall displacement occur as VT deteriorates into VF. A displacement parameter is therefore used in some embodiments, which will be described in greater detail below, as an additional factor included in criteria set for detecting and classifying an arrhythmia.

By corroborating electrical event data with mechanical event data, controller 110 is able to reliably detect arrhythmias, even if electrical signals obtained are of relatively poorer quality than conventional EGM signals obtained from the right ventricular apex. The detection of an arrhythmia and classification of the arrhythmia based on the parameterized mechanical and electrical event data can be used to trigger the delivery of an appropriate therapy. Therapy control circuit 112 may select a type of electrical stimulation therapy based on the arrhythmia detection and classification provided by controller 110. For a review of arrhythmia therapies, reference is made to the above-cited '186 patent issued to Olson. Therapy control circuit 112 may select bradycardia pacing, anti-tachycardia pacing, cardioversion or defibrillation and controls the selection of electrodes for delivering electrical pulses via electrode selector 102, the pulse amplitudes, various timing intervals, and other parameters used in controlling the therapy delivered by therapy delivery system 114. Therapy control circuit 112 may alternatively select and control other types of therapies such as drug delivery, to be delivered by therapy delivery system 114. Thus therapy delivery system may take the form of an electrical pulse generator or a drug delivery pump.

Controller 110 may also control a telemetry circuit 116 to communicate a record of detected arrhythmia episodes to an external device via antenna 118. The external device, which may be a programmer, may display EGM/ECG and accelerometer derived data stored at the time of arrhythmia detection and for an interval thereafter for review by a clinician. Storage of EGM-based arrhythmia episode data and telemetric communication of such data is known in the art.

Figure 3:
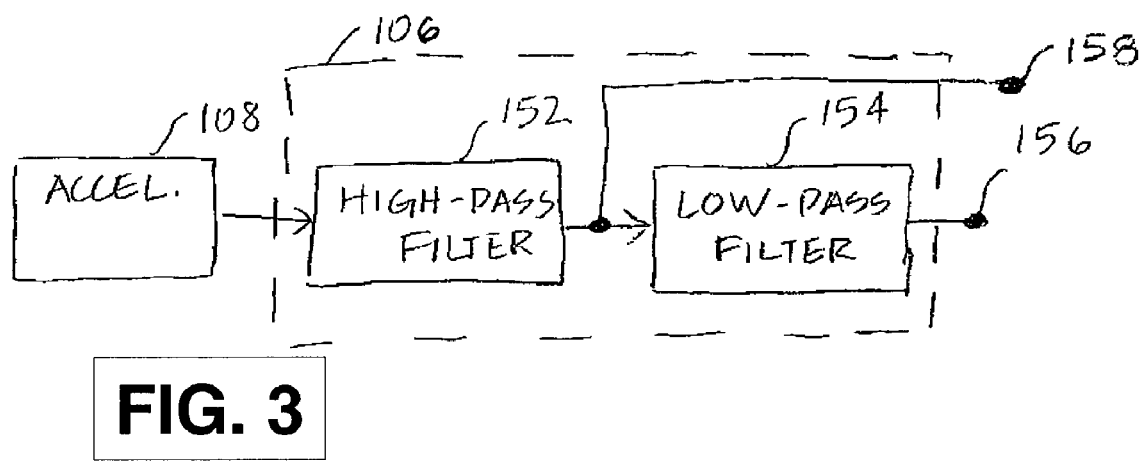
FIG. 3 is a diagram of circuitry that may be included in the signal processor circuit shown in FIG. 2 for obtaining both an acceleration signal and a displacement signal from a sensed accelerometer signal.

FIG. 3 is a diagram of circuitry that may be included in signal processor circuit 106 for obtaining both an acceleration signal and a displacement signal from a sensed accelerometer signal. The signal from an accelerometer 108 is received by signal processing circuit 106 and first passed through a high-pass filter 152 to eliminate low frequency, non-cardiac related motion, such as body motion or respiratory motion. The output of high-pass filter 152 is provided as an acceleration signal 158 which may be further processed as described above by circuitry included in signal processing circuit 106 or by controller 110. The output of high-pass filter 152 is additionally provided as input to a low-pass filter 154 to obtain the low frequency component of the acceleration signal. The low frequency component of the acceleration signal provides a reliable estimate of cardiac wall displacement. The output of low-pass filter 154 is therefore provided as a displacement signal 156, which may be further processed as described above by signal processing circuit 106 or controller 110. In one embodiment, high-pass filter 152 is provided as an approximately 0.05 Hz high-pass filter, and low-pass filter 154 is provided as an approximately 3 Hz low-pass filter. By obtaining a displacement signal from the low-frequency components of the acceleration signal, a reliable estimate of cardiac wall displacement can be obtained. Signal processing time and power requirements for deriving cardiac wall displacement from an accelerometer signal may be reduced compared to other methods such as performing a double-integration of the acceleration signal.

Figure 4:
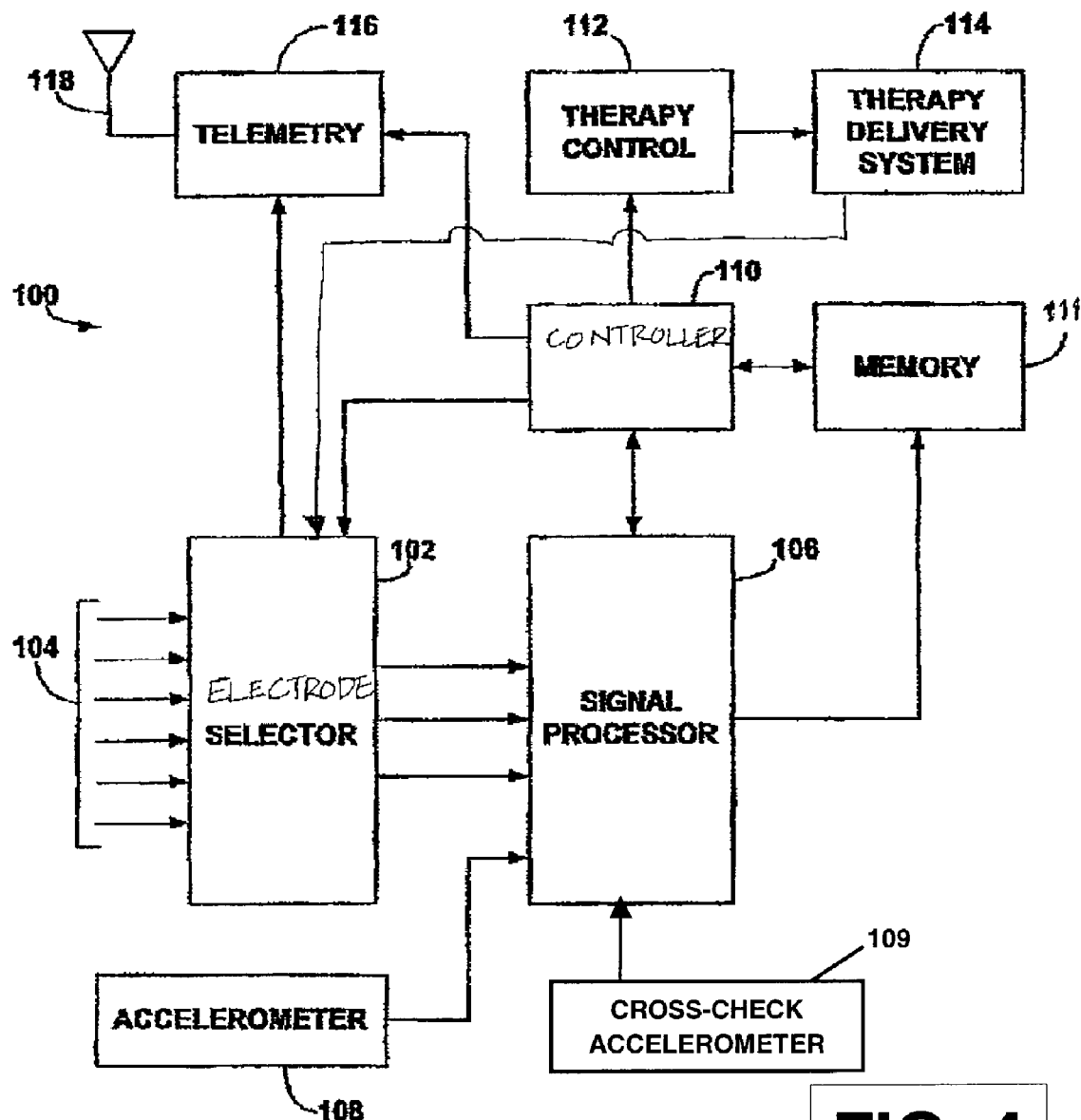
FIG. 4 is a block diagram illustrating an alternative embodiment of a system for detecting cardiac arrhythmias.

FIG. 4 is a block diagram illustrating an alternative embodiment of a system for detecting cardiac arrhythmias. In this embodiment, an additional accelerometer 109 is provided as a cross-check sensor to detect and eliminate non-cardiac related noise from the signal received by the primary accelerometer 108. The cross-check accelerometer 109 is positioned at a separate location from primarily accelerometer 108. Cross-check accelerometer 109 may be located in or on a device housing or connector block such as those shown in FIG. 1. Alternatively, cross-check accelerometer 109 may be located on a separate lead or on the same lead as primary accelerometer 108 but at a proximal location from primary accelerometer 108. Large signals that are received concurrently from both the primary accelerometer 108 and the cross-check accelerometer 109 may be rejected by signal processor circuit 106 as non-cardiac motion artifact.

In alternative embodiments that include a single accelerometer, as shown in FIG. 2, rejection of non-cardiac motion artifact may be handled by imposing cardiac-related physiologic limits on the received accelerometer signal. Signals outside the cardiac-related physiologic upper and/or limits of amplitude and/or frequency are rejected as non-cardiac motion artifact by signal processor circuit 106.

Figure 5:
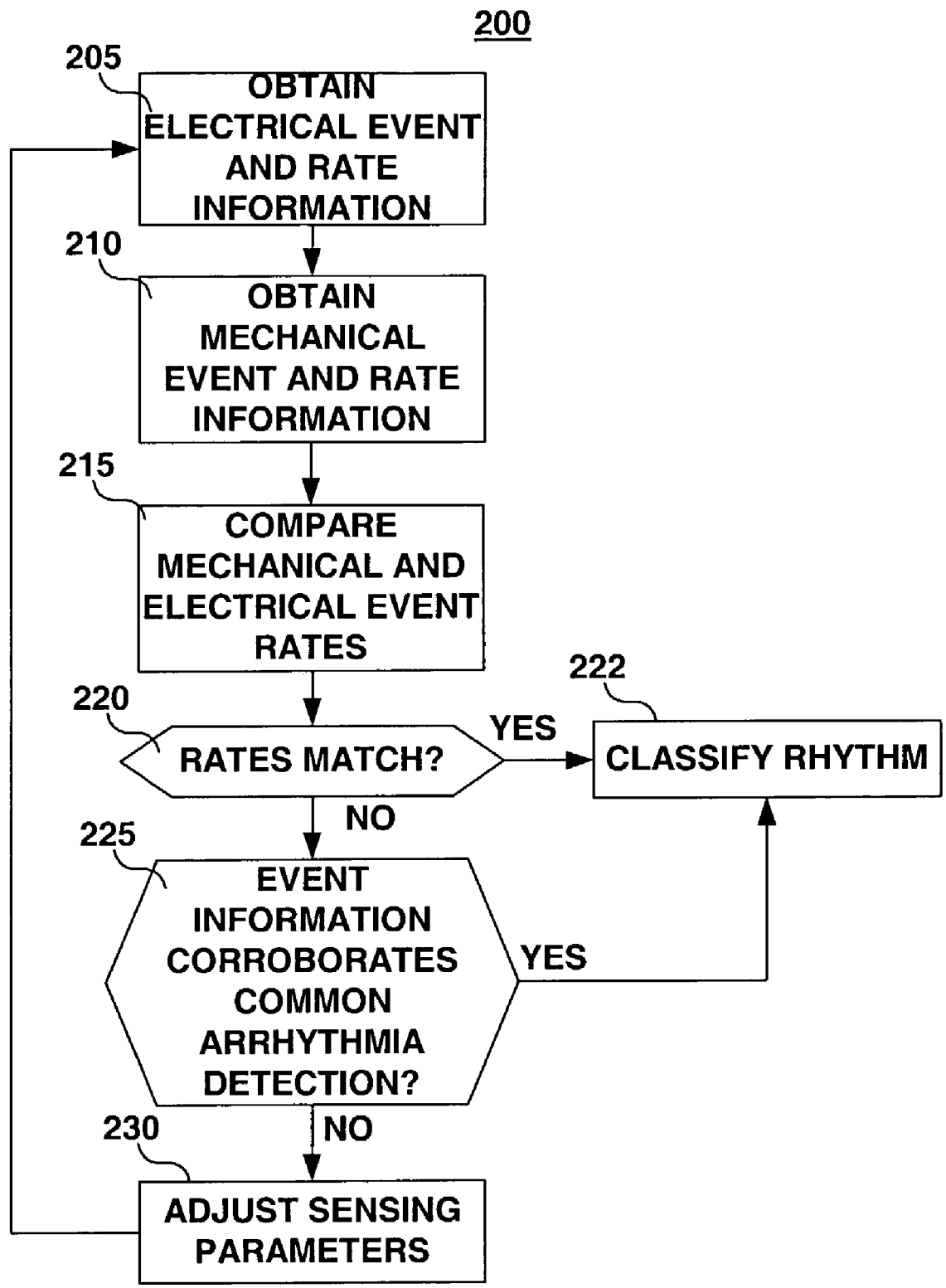
FIG. 5 is a flow chart providing an overview of a method for detecting arrhythmias based on sensing electrical and mechanical cardiac activity according to one embodiment of the present invention.

FIG. 5 is a flow chart providing an overview of a method for detecting arrhythmias based on sensing electrical and mechanical cardiac activity according to one embodiment of the present invention. At step 205, electrical event information is obtained which may include the event rate, such as the ventricular rate based on intervals measured between sensed R-waves, and may further include other parameterized EGM/ECG signal data such as amplitude and interval variability. The rate measurement may for example be an instantaneous measurement or a calculation over time, such as an average rate or a median of a defined number of beats. At step 210, mechanical event information is obtained, which may include the event rate, such as the rate of accelerations determined from intervals measured between sensed acceleration events, and may further include other parameterized accelerometer or other mechanical sensor signal data such as acceleration event amplitudes and amplitude and rate variability.

At step 215, the mechanical event rate and the electrical event rate are compared to allow a determination of the correlation of the event rates at decision step 220. If the rates match, e.g. if the rates are within a specified amount of each other, the rhythm is classified based on the event rate at step 222.

If the rates do not match, additional parameterized mechanical and electrical event information is examined at decision step 225 to determine if the parameterized electrical and mechanical event data corroborate a common arrhythmia detection. If so, the arrhythmia is detected and classified at step 222. If the event information does not corroborate a common arrhythmia detection, either or both the EGM/ECG signal and the accelerometer or other mechanical sensor signal may be under or oversensing electrical and mechanical events, respectively. Therefore, at step 230, parameters controlling the sensing operations of either or both electrical and mechanical event sensing may be adjusted. After adjusting sensing parameters, method 200 is repeated.

Figure 6A:
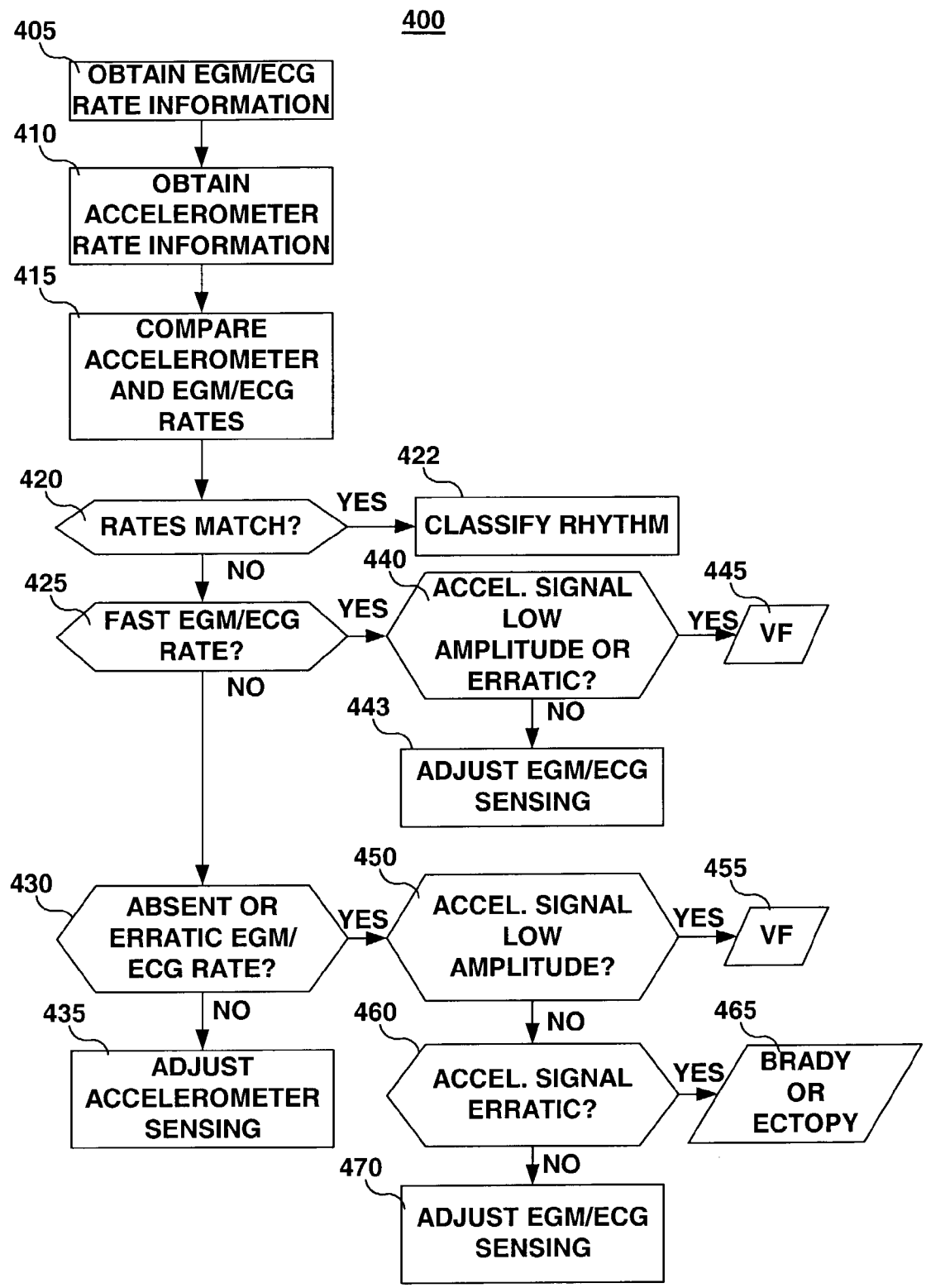
FIG. 6A is a flow chart summarizing in greater detail steps included in the method of FIG. 5 for detecting arrhythmias according to the present invention.

FIG. 6A is a flow chart summarizing in greater detail steps included in a method for detecting arrhythmias according to the present invention. Method 400 is described with regard to the detection of ventricular arrhythmias, however, it is recognized that methods described herein may be applied for the detection of atrial arrhythmias as well. Beginning at step 405, ventricular electrical event information is obtained from a sensed from an EGM or ECG signal, which may be sensed from any desired sensing vector selected from available electrode pairs. Selected electrode pairs may or may not be located on the same lead or in the same location as an accelerometer or other mechanical sensor of cardiac activity.

At step 410, ventricular mechanical event information is obtained from an accelerometer or other mechanical sensor of ventricular wall motion. A rate may be derived from an accelerometer signal by measuring the interval between sensed acceleration events. Electrical and mechanical event rates may be determined on a beat-by-beat or less frequent basis and may be determined for each consecutive event, as an average of a number of detected R-R and acceleration intervals, or as a running average of a specified number of consecutive intervals. When the EGM/ECG and accelerometer measured ventricular rates are determined at steps 405 and 410, additional information may be determined and stored such as the variability of the measured intervals, measured amplitudes of the R-wave and acceleration events, or other parameterized data for use in determining the regularity of sensed events in amplitude and/or time. Alternatively, a number of event intervals and amplitudes may be temporarily stored for further analysis later on if a disparity exists in the EGM/ECG and accelerometer measured rates.

At step 415, the accelerometer and EGM/ECG measured rates are compared. If the rates match, as determined at decision step 420, the rate is used in classifying the ventricular rhythm at step 422. The rates may be determined to match if the EGM/ECG rate and the accelerometer rate are within a specified percentage of each other or within a specified number of beats per minute, for example within 5 to 10 beats per minute. If the rates match, the EGM/ECG and accelerometer indicated rates are deemed reliable for use in rhythm classification. Rhythm classifications may include bradycardia, sinus rhythm, sinus tachycardia, or ventricular tachycardia according to the measured rate.

If, however, the measured accelerometer and EGM/ECG rates do not match, as determined at decision step 420, further analysis of the two signals is required before rhythm classification is possible. At step 425, method 400 determines if the EGM/ECG measured rate is fast. A fast EGM/ECG rate is detected when the measured electrical events, e.g., R-R intervals, are shorter than a programmed arrhythmia detection criteria, for example when a majority of intervals, such as 75% of the intervals, are shorter than 300 ms.

If the EGM/ECG rate is fast, as determined at decision step 425, and the accelerometer or other mechanical wall motion sensor signal is of low amplitude, silent or erratic, as determined at decision step 440, ventricular fibrillation (VF) is detected at step 445. Erratic signal behavior is identified when event amplitudes or event intervals change dramatically over a short period of time. For example, the difference between the maximum and minimum event amplitudes and/or event intervals determined from a predetermined number of consecutively sensed events may be used in identifying erratic behavior. The fast EGM/ECG rate corroborated by the absence of sensed mechanical activity or only erratic or low amplitude mechanical events evidences VF or perhaps polymorphic ventricular tachycardia. The VF detection may then be used by the IMD for selecting and delivering an appropriate arrhythmia therapy according to methods known in the art.

If the accelerometer or other mechanical wall motion sensor derived rate is regular at step 440 but didn't match the fast EGM/ECG sensed rate as determined previously at step 420, an error in the measurement of EGM/ECG rate, such as double counting due to sensing of both R-waves and T-waves during each cardiac cycle or, in the case of an atrial EGM/ECG measurement, sensing of both P-waves and subsequent far field R-waves during each cardiac cycle. In this case the IMD may adjust the sensitivity to EGM/ECG signals at step 443 to eliminate the noise source and restore accurate sensing.

If the EGM/ECG rate is not determined to be fast at step 425, and is determined to be absent or erratic at decision step 430, the accelerometer signal is examined at step 450. If the accelerometer or other mechanical wall motion signal is of low amplitude, VF detection is made at step 455. Absence of regular mechanical activity and absent or erratic EGM/ECG events evidence VF, which detection can then be used for selecting an appropriate therapy.

If the accelerometer or other mechanical wall motion sensor is not of low amplitude (step 450) but is identified as erratic at decision step 460, bradycardia or ectopy is detected at step 465. Erratic mechanical activity coupled with erratic or absent electrical activity evidences bradycardia or ectopy. Such detection may then be used in triggering an appropriate therapy such as bradycardia pacing.

If regular mechanical activity is being sensed, producing negative results to the decision steps 450 and 460 for identifying low amplitude or erratic accelerometer signals, respectively, then a normal sinus rhythm may be present. The EGM/ECG signal may be contaminated with noise or otherwise inaccurate due to undersensing or oversensing, producing an erratic or absent EGM/ECG rate. Therefore, at step 470, parameters controlling the EGM or ECG sensing operations are adjusted. The EGM/ECG sensing parameters that are adjusted may include the sensing electrodes used, the EGM/ECG amplifier gain or sensitivity. Adjustments may be made automatically until an EGM/ECG measured rate matches the mechanical event rate.

Likewise, if the EGM/ECG signal is determined to be slow and regular, resulting in negative results to decision steps 425 and 430 for detecting fast or absent or erratic EGM/ECG signals, respectively, the accelerometer or other mechanical wall motion sensor signal may be under- or oversensing. A slow EGM/ECG rate is a rate less than the slowest tachycardia detection rate. A regular EGM/ECG rate may be defined as an average rate that does not change by more than a specified amount within a given number of cardiac cycles or a rate in which consecutive cycle intervals do not vary by more than a specified amount.

When the EGM/ECG rate is slow and regular and the accelerometer rate does not match this rate, the accelerometer sensing parameters are adjusted at step 435. Accelerometer sensing parameters that may be adjusted include a gain setting, or sensitivity or threshold setting. Automatic adjustments to accelerometer sensing parameters may be performed until the measured mechanical event rate matches the EGM/ECG event rate. It is recognized that if electromechanical disassociation is present, the accelerometer sensing parameters cannot be adjusted in a way to produce an accelerometer measured rate that matches an EGM/ECG rate.

Figure 6B:
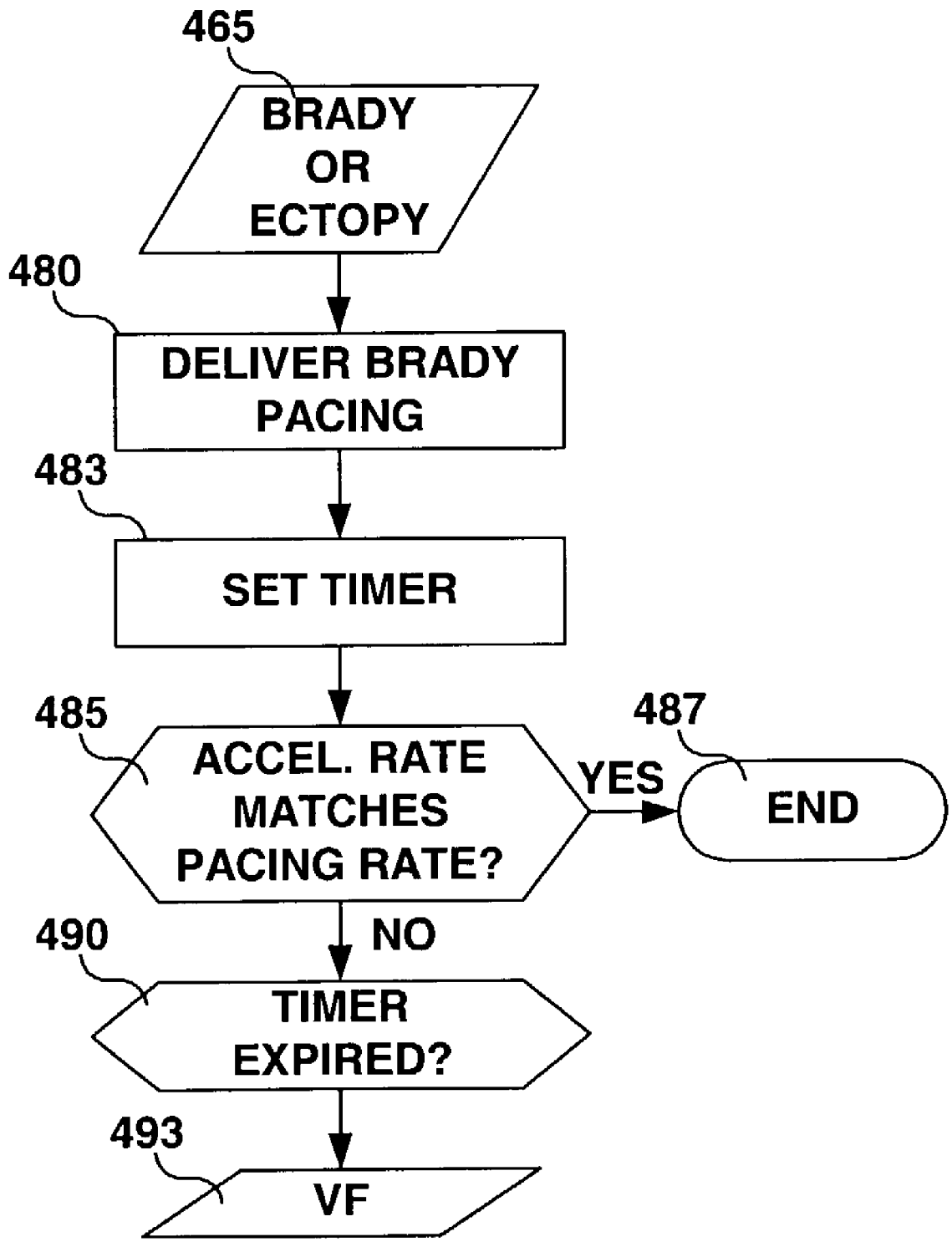
FIG. 6B is a flow chart of a safety feature for providing appropriate therapies in cases of ambiguous EGM/ECG and accelerometer signals.

FIG. 6B is a flow chart summarizing steps included in a safety feature for providing appropriate therapies in cases of ambiguous EGM/ECG and accelerometer signals. It is noted that, in some instances, sensed EGM/ECG and accelerometer signals may be ambiguous in detecting the conditions of VF and bradycardia. Therefore, if a bradycardia detection is made as indicated at step 465 and bradycardia pacing is delivered at step 480, a timer is set at step 483 to a predetermined interval of time.

If the accelerometer measured rate does not match the bradycardia pacing rate delivered by the IMD (implying no ventricular pacing capture), as determined at decision step 485, before expiration of the timer as determined at step 490, the IMD automatically reverts to a VF classification at step 493. This revised classification may be used by the IMD to select and deliver appropriate defibrillation therapy. If the accelerometer measured rate does match the pacing rate, the bradycardia detection is correct and the appropriate therapy is being delivered. No further action is required so the method is terminated at step 487.

Figure 7:
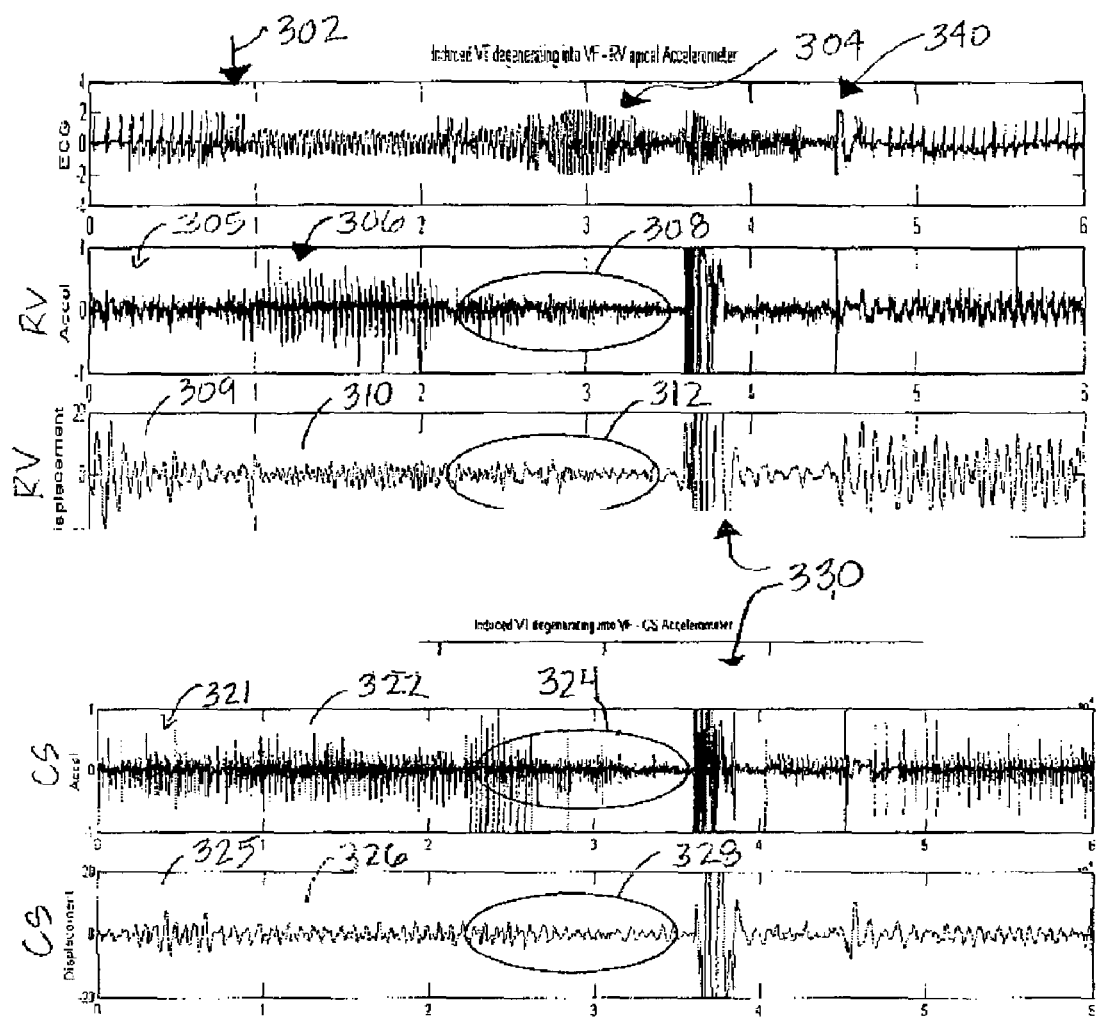
FIG. 7 shows sample recordings of an ECG signal contemporaneously acquired with acceleration and displacement signals obtained from an accelerometer positioned in the right ventricle and in the coronary sinus.

FIG. 7 shows recordings of an ECG signal contemporaneously acquired with acceleration and displacement signals obtained from an accelerometer positioned in the right ventricle and in the coronary sinus. Ventricular tachycardia (VT) is induced at 302. The right ventricular acceleration signal (RV Accel) and the coronary sinus acceleration signal (CS Accel) are seen to increase in amplitude during VT, at 306 and 322 respectively, compared to the acceleration signals 305 and 321 during ventricular pacing.

The RV and CS displacement signals are obtained by filtering the RV and CS acceleration signals, respectively, using a high-pass and a low-pass filter. The RV and CS displacement signals during VT, 310 and 326, respectively, are seen to decrease in amplitude compared to the respective displacement signals during normal pacing, 309 and 325. The induced VT is observed on the ECG signal to deteriorate into VF at 304. The RV acceleration signal, the RV displacement signal, the CS acceleration signal, and the CS displacement signal are all observed to decrease in amplitude during the transition to VF at 308, 312, 324, and 328, respectively, and remain at low amplitudes until the VF is terminated at 340. The dynamic changes in acceleration and displacement during the transition from a hemodynamically stable rhythm to a hemodynamically unstable rhythm may therefore be used to quickly detect a deteriorating arrhythmia.

At 330, large amplitude signals due to motion artifact are observed on both the RV and CS accelerometer signals. This motion artifact, appearing on both accelerometer signals is rejected during signal processing. In a single-accelerometer system, the large amplitude of the motion artifact signals would exceed a physiological limit specified to reject non-cardiac related motion.

Figure 8:
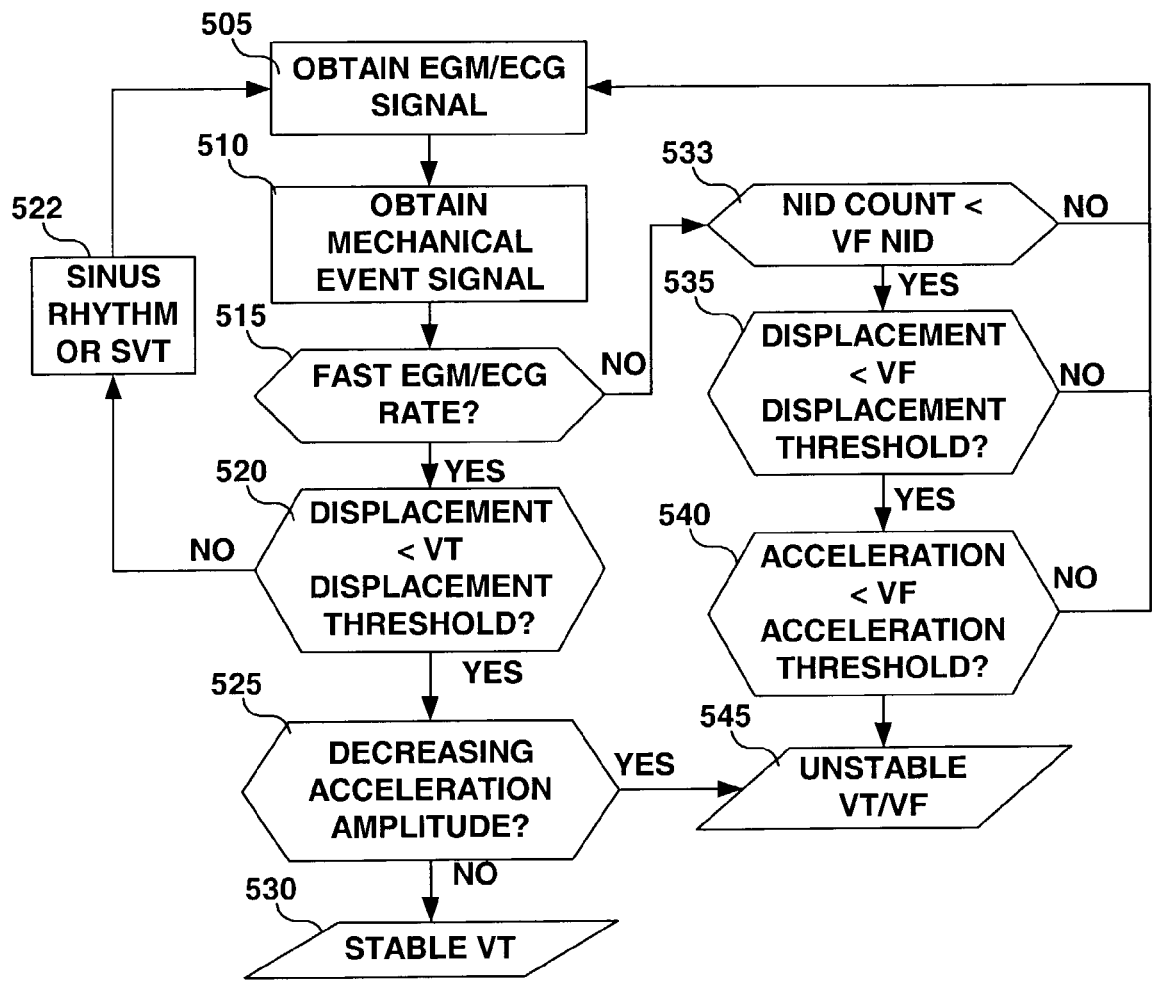
FIG. 8 is a flow chart of an alternative method for detecting arrhythmias based on mechanical and electrical event data.

FIG. 8 is a flow chart summarizing steps included in an alternative method for detecting arrhythmias based on mechanical and electrical event data. Method 500 advantageously monitors dynamic changes in acceleration signals and/or displacement signals for detecting the transition from hemodynamically stable rhythms to unstable tachycardia or fibrillation. Ventricular tachycardia and ventricular fibrillation may occur at overlapping rates, therefore, rate information alone may not be adequate in discriminating between tachycardia and fibrillation, particularly in discriminating between hemodynamically stable and unstable forms of VT. Thus, in the embodiment shown in FIG. 8, displacement and acceleration measurement parameters are determined for dynamically monitoring cardiac mechanical function and corroborating EGM/ECG data in arrhythmia detection.

At step 505, an EGM/ECG signal is obtained for monitoring the rate of electrical events as described previously. At step 510, a mechanical event signal is obtained, preferably a signal received from a coronary sinus lead-mounted accelerometer, from which the magnitude of cardiac wall acceleration and cardiac wall displacement can be estimated. As described previously, a displacement signal is preferably obtained by filtering the accelerometer signal to obtain the low frequency component of an acceleration signal. Alternatively, displacement may be obtained by integrating the accelerometer signal twice. For example, methods for obtaining a displacement estimate may be performed as generally described in the above-cited '412 patent to Mouchawar.

If a fast rate is detected from the EGM/ECG signal, as determined at decision step 515, the changes in a displacement measurement parameter are evaluated at step 520. Fast EGM/ECG rate detection criteria may be based on a threshold R-R interval cycle length and a minimum number of intervals shorter than the R-R interval cycle length. Upon detecting a fast EGM/ECG rate, the displacement measurement is compared to a VT displacement threshold. During VT, displacement decreases as shown in the sample recordings of FIG. 7. Therefore, a VT displacement threshold may be specified, below which the displacement measurement supports a detection of VT.

A measurement of displacement may be determined as a peak amplitude or peak-to-peak difference of the double-integrated or filtered acceleration signal during a cardiac cycle or averaged over a number of cardiac cycles. In one embodiment, an average of the peak-to-peak difference of the displacement signal is measured during each of four consecutive cardiac cycles and compared to a specified VT displacement threshold. If the displacement measurement is not less than the VT displacement threshold, method 500 returns to step 505 to continue monitoring the EGM/ECG signal. The elevated EGM/ECG rate is determined to be sinus tachycardia or supraventricular tachycardia (SVT), as indicated at step 522, therefore, no ventricular arrhythmia detection is made and no ventricular interventional therapy is required. It is recognized that additional criteria may be applied to the EGM/ECG signal information to identify an SVT, for example as disclosed in the above-cited '186 patent to Olson et al., for use in selecting an appropriate atrial therapy.

If, however, the displacement parameter crosses the VT displacement threshold, as determined at decision step 520, changes in an acceleration measurement parameter are examined at decision step 525. If the acceleration measurement parameter is decreasing, the fast rate is deteriorating into a hemodynamically unstable VT or VF, which is detected at step 545. This unstable VT/VF detection may be used by an IMD for selecting an arrhythmia therapy.

An acceleration measurement parameter evaluated at step 525 may be determined as the peak amplitude or peak-to-peak difference of the accelerometer signal during one cardiac cycle or averaged over a number of consecutive cardiac cycles. In one embodiment, the peak-to-peak difference of the accelerometer signal during each of a given number of consecutive cardiac cycles, e.g. four cardiac cycles, is averaged to determine an acceleration measurement parameter. This parameter is compared to the most previous determined average, which may be a running average. If the current average is less than the previous average by a specified amount, the cardiac wall acceleration is determined to be decreasing. Alternatively, the acceleration parameter may be compared to a specified unstable VT/VF acceleration threshold, below which unstable VT/VF is indicated.

If the acceleration measurement parameter is not found to be decreasing at decision step 525, stable VT is detected as indicated by step 530. The VT may be stable, but, based on the decreased displacement detected at decision step 520, the patient may be hemodynamically compromised. Detection of stable VT, therefore, may be used by an IMD for selecting an appropriate interventional therapy.

During some arrhythmia episodes, the EGM/ECG arrhythmia detection criteria may not be fully satisfied due to undersensing of the relatively low amplitude depolarizations that can occur during arrhythmias, in particular during fibrillation. Monitoring of dynamic changes in the acceleration and/or displacement signals may be used for verifying the heart rhythm periodically or whenever an arrhythmia is suspected based on inconclusive EGM/ECG rate data. For example, short or erratic EGM/ECG cycle lengths may be measured during VF, but criteria regarding the required number of intervals less than an arrhythmia detection interval may not be met due to EGM/ECG undersensing.

Thus, if fast EGM/ECG rate detection criteria are not met at decision step 515, but short cycle lengths have been detected causing a number of intervals to detect (NID) counter to register a value less than the required number of intervals to detect (NID) VF as determined at decision step 533, displacement and acceleration information may be examined to verify that EGM/ECG undersensing of VF is not present by proceeding to step 535. At decision step 535, the displacement measurement parameter, which may be determined as described above, is compared to a predefined VF displacement threshold. If the displacement parameter is not less than the VF displacement threshold, then VF is not present, and method 500 returns to step 505.

If the displacement parameter is less than the VF displacement threshold, the acceleration measurement parameter, which may be determined as described above, is compared to a VF acceleration threshold at decision step 540. If the acceleration parameter is less than the VF acceleration threshold, a detection of unstable VT/VF is made at step 545. This detection may be used by the IMD to select an arrhythmia therapy. Thus, monitoring dynamic changes in a displacement signal and an acceleration signal allow VF to be detected despite EGM/ECG undersensing of fibrillation waves.

Method 500 demonstrates an algorithm for monitoring dynamic changes in cardiac wall displacement and acceleration as transitions in the heart rhythm occur. Arrhythmia detection and classification criteria according to this embodiment therefore require defining displacement change thresholds and optionally acceleration change thresholds that discriminate the rhythm types to be detected. A displacement measurement parameter and an acceleration measurement parameter determined from an acceleration signal and a displacement signal, respectively, are compared to the predefined criteria for detecting rhythm changes. As shown in FIG. 8, detection of the transition from hemodynamically stable VF to unstable VT/VF is based on criteria including a decreasing acceleration measurement parameter and a displacement less than a specified threshold. It is recognized that other arrhythmia detection criteria may be defined which include factors relating to dynamic changes in an acceleration signal and/or displacement signal and may further include EGM/ECG-related factors.

Figure 9:
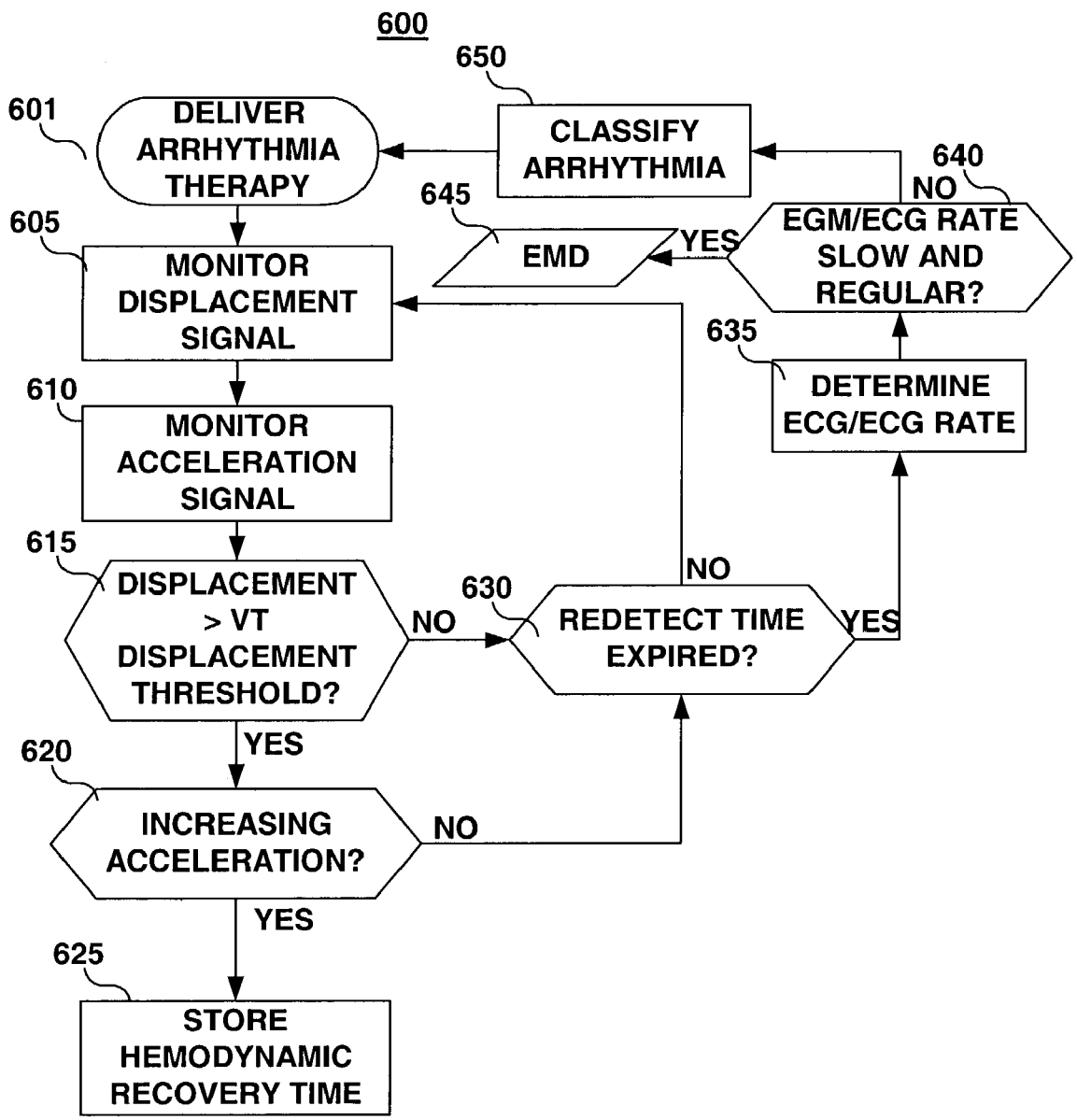
FIG. 9 is a flow chart of a method for evaluating the efficacy of an arrhythmia therapy in providing electrical and mechanical recovery.

FIG. 9 is a flow chart summarizing steps included in a method for evaluating the efficacy of an arrhythmia therapy in providing electrical and mechanical recovery. Method 600 is initiated upon the delivery of an arrhythmia therapy at step 601, which may be an electrical stimulation therapy such as anti-tachycardia pacing therapy, or a cardioversion or defibrillation shock or a drug therapy, delivered in response to an arrhythmia detection. At steps 605 and 610, the displacement signal and the acceleration signal, respectively, are monitored and a displacement measurement parameter and accelerometer measurement parameter are determined for comparisons to hemodynamically unstable arrhythmia criteria at steps 615 and 620.

At decision step 625, the displacement parameter is compared to a VT displacement threshold. If the displacement parameter remains less than the VT displacement threshold, and a re-detection timer or interval counter has not yet expired as determined at decision step 630, method 600 returns to step 605 to continue monitoring the displacement and acceleration signals. If the displacement parameter has increased to a value greater than the VT displacement threshold, the acceleration parameter may be evaluated to determine if acceleration is increasing, indicating a transition back to a hemodynamically stable rhythm. If the acceleration parameter is increasing, as determined at decision step 620, hemodynamic recovery has been reached, and the time to reach hemodynamic recovery from the initiation of the arrhythmia therapy at step 601 may be stored in memory. Stored arrhythmia episode data along with post-therapy hemodynamic recovery times may provide useful information to clinicians and researchers in evaluating the effectiveness of an arrhythmia therapy, selecting programmable arrhythmia therapy options, and in understanding the hemodynamic consequences during an arrhythmia, during therapy delivery, and during a post-therapy recovery period.

If the displacement and acceleration parameters have not exceeded the hemodynamically unstable VT/VF criteria applied at decision steps 615 and 620, and a redetection timer or interval counter has expired as determined at decision step 630, a redetection and classification of the arrhythmia may be made at step 650. Such a redetection may also be based on the EGM/ECG rate determined at step 635. If the EGM/ECG rate is not slow and regular, as determined at decision step 640, an arrhythmia redetection is made, and the arrhythmia may be classified according to displacement and acceleration parameters and EGM/ECG rate. If, however, the EGM/ECG rate is slow and regular, i.e. less than the lowest arrhythmia detection rate, than electro-mechanical dissociation is detected at step 645. This information is stored for diagnostic and monitoring purposes and may be used to select or modify therapy delivery parameters.

Some of the techniques described above may be embodied as a computer-readable medium including instructions for a programmable processor such as processor 106 or controller 110 shown in FIGS. 2 and 4. The programmable processor may include one or more individual processors, which may act independently or in concert. A "computer-readable medium" includes but is not limited to read-only memory, Flash memory and a magnetic or optical storage medium. The medium includes instructions for causing a processor to perform the method for detecting arrhythmias in an implantable medical device, described above.

Thus, a system and method for detecting and classifying arrhythmias have been described in which evidence of arrhythmias from sensed mechanical activity is used to corroborate sensed electrical activity. It is recognized that numerous variations to the algorithms described above may exist in which mechanical and electrical information is gathered for detecting and classifying an arrhythmia. While the present invention has been described according to specific embodiments presented herein, these embodiments are intended to be exemplary, not limiting, with regard to the following claims.

The invention claimed is:

1. An implantable medical device, comprising:
   a plurality of electrodes for detecting electrical events of a patient;
   a sensor for detecting mechanical events of the patient;
   a controller receiving signals, indicative of the detected electrical events, from the plurality of electrodes, and receiving signals, indicative of the detected mechanical events, from the sensor;
   the controller analyzing an amplitude, a rate, and a variability of the amplitude and the rate of the electrical event signals and the mechanical event signals, and comparing the rate of the electrical event signals with the rate of the mechanical event signals; and
   the controller selecting a therapy and controlling the therapy delivered by the device to the patient in response to the comparison of the rate of the electrical event signals with the rate of the mechanical event signals, and, if the rate of the electrical event signals does not match the rate of the mechanical event signals, in response to the analysis of each of the signals, wherein the controller adjusts one of a sensing sensitivity corresponding to the detecting by the plurality of electrodes, if the rate of the electrical event signals does not match the rate of the mechanical event signals and the electrical event signals are fast and the mechanical event signals are not one of low amplitude and erratic, and a sensing sensitivity corresponding to the detecting by the sensor if the rate of the electrical event signals does not match the rate of the mechanical event signals and the rate of the electrical event signals is not fast and is not one of absent and erratic.

2. The device of claim 1, wherein the mechanical event signals correspond to cardiac wall displacement.

3. The device of claim 2, further comprising a filter matching a low frequency component of a cardiac wall acceleration corresponding to displacement.

4. The device of claim 1, wherein the sensor is positioned along the left ventricle of the patient.

5. The device of claim 1, further comprising a coronary sinus lead, wherein the sensor is positioned along the coronary sinus lead.

6. The device of claim 1, further comprising a cross-check sensor detecting the mechanical activity, wherein the controller rejects the mechanical events if detected by both the sensor and the cross-check sensor.

7. The device of claim 1, wherein the controller further controls an electrode selection circuit to select a desired electrode pair from the plurality of electrodes for acquisition of the electrical event signals.

8. The device of claim 1, wherein the controller controls the therapy delivered by the device by selecting one or more electrodes from the plurality of electrodes to deliver the therapy.

9. The device of claim 1, wherein the therapy is selected from a group of therapies including bradycardia pacing, anti-tachycardia pacing, cardioversion and defibrillation.

10. The device of claim 1, wherein the mechanical event signals correspond to cardiac wall acceleration.

11. A method for detecting arrhythmias in an implantable medical device, comprising:
    detecting electrical event signals of a patient;
    detecting mechanical event signals of the patient;

analyzing an amplitude, a rate, and a variability of the amplitude and the rate of the electrical event signals and the mechanical event signals;

comparing the rate of the electrical event signals with the rate of the mechanical event signals;

selecting a therapy and controlling the therapy delivered by the device to the patient in response to the comparison of the rate of the electrical event signals with the rate of the of the mechanical event signals and, if the rate of the electrical event signals does not match the rate of the mechanical event signals, in response to the analysis of each of the signals; and adjusting a sensing sensitivity for the detecting of the electrical event signals if the rate of the electrical event signals does not match the rate of the mechanical event signals and the electrical event signals are fast and the mechanical event signals are not one of low amplitude and erratic.

12. The method of claim 11, wherein the mechanical event signals correspond to cardiac wall displacement.

13. The method of claim 11, wherein the therapy is selected from a group of therapies including bradycardia pacing, anti-tachycardia pacing, cardioversion and defibrillation.

14. The method of claim 11, wherein the mechanical event signals correspond to cardiac wall acceleration.

15. A method for detecting arrhythmias in an implantable medical device, comprising:

detecting electrical event signals of a patient;

detecting mechanical event signals of the patient;

analyzing an amplitude, a rate, and a variability of the amplitude and the rate of the electrical event signals and the mechanical event signals;

comparing the rate of the electrical event signals with the rate of the mechanical event signals;

selecting a therapy and controlling the therapy delivered by the device to the patient in response to the comparison of the rate of the electrical event signals with the rate of the of the mechanical event signals and, if the rate of the electrical event signals does not match the rate of the mechanical event signals, in response to the analysis of each of the signals; and adjusting a sensing sensitivity for the detecting of the mechanical event signals if the rate of the electrical event signals does not match the rate of the mechanical event signals and the rate of the electrical event signals is not fast and is not one of absent and erratic.

* * * * *